United States Patent [19]

Austin

[11] Patent Number: Plant 7,213

[45] Date of Patent: Apr. 3, 1990

[54] ROSE PLANT 'AUSSPRY'

[75] Inventor: David C. H. Austin, Albrighton, England

[73] Assignee: David Austin Roses, Albrighton, England

[21] Appl. No.: 259,280

[22] Filed: Oct. 18, 1988

[51] Int. Cl.[4] ..... A01H 5/00
[52] U.S. Cl. ..... Plt./1
[58] Field of Search ..... Plt./1

[56] References Cited

PUBLICATIONS

Meikle, C. E. (Ed.) *Modern Roses* 8, The McFarland Co., Harrisburg, Pa., U.S.A. 1980, p. 477 relied on.

*Primary Examiner*—James R. Feyrer
*Attorney, Agent, or Firm*—Ladas & Parry

[57] ABSTRACT

A new variety of rose plant of the shrub class distinctive in its character by its large double flowers with open centers exposing a bunch of golden stamens with abundant, continual blooming and the unusual blend of coloring and shaping of the flower.

1 Drawing Sheet

BACKGROUND OF THE INVENTION

The present invention relates to a new and distinct variety of shrub rose, a seedling resulting from a definite effort to produce an improvement in this class of roses.

Primary features of this new variety which connote a distinctive advance over existing types are the vigorous abundant and continual blooming taken with the perfection of the fully double flowers of an old-fashioned type more particularly apparent in the accompanying illustration of a specimen thereof.

BRIEF SUMMARY OF THE INVENTION

The following is a detailed description of the new variety, colour terminology being in accordance with the "Methuen Handbook of Colour" published by Eyre Methuen Ltd. (1963).

BRIEF DESCRIPTION OF DRAWING

The drawing is a colour photographic representation of my new variety in a flush of bloom taken substantially in side view and showing inflorescence in various stages, stems and foliage of the plant.

DETAILED BOTANICAL DESCRIPTION

Variety denomination (in accordance with the UPOV Convention): Ausspry

Type: Hardy; bush; outdoor; seedling; for cut flowers and garden decoration.

Class: Shrub.

Propagation: Holds its distinguishing characteristics through succeeding propagations by budding.

The rose plant was grown at Albrighton, Nr. Wolverhampton, England and was derived as follows:

Female parent (seed parent): Lilian Austin.
Male parent (pollen parent): Chaucer.

The operation of the artificial pollination is therefore expressed by the following (Lilian Austin × Chaucer).

The following observations are made of specimens grown outdoors in England.

Plant Description

Plant:

*Height.*—120 cm. on average.

*Habit.*—Dense and bushy.

Main stem:

*Thorns.*—Very thorny, varying in size from very small to very large, slightly recurved.

*Colour.*—The thorns are red 10D 8 on young stems becoming brown 7E 8 upon ageing.

Branches:

*Colour.*—Young stems: Deep green 29 E8. Adult wood: Dark green 29 F8.

Leaves:

*Stipules.*—Medium width — Medium Green glandular hairy with Dark green wings.

*Petiol.*—Upper side — Concave, Mid-Green. Under side — Light Green with glandular hairs and occasional small prickles.

*Folioles.*—3, 5 most common. Shape — Broadly ovate. Serration — dentate with Red tips. Texture — Slightly ruglose — rough on under side.

*General effect.*—Dense Dark green, Mattish.

*Colour.*—Young foliage — Upper side — Olive Green 3 D8 overlaid red. Under side — Very Dark Red 11 E7. Adult foliage — Upper side — Dark Green 29 F8. Under Side — Dark Green 29 F6.

*Hips and seeds.*—This variety does not produce seeds in normal garden conditions, but only when cross-pollinated.

The inflorescence is:

Number of flowers: A high percentage of solitary flowers. Most stems present one primary and up to three small buds bunched in tight cluster.

Peduncle: Straight, Rigid, Light green tinged Red — numerous Red aciculas.

Length: 5½ cm on average.

Sepals: Upper side: Light green, very short fine hairs. Under side: Medium green, occasional glandular hairs and either finely hairy or glandular hairy at edges. Occasional narrow lobes.

Bud:

*Shape.*—Ovate pointed.
*Length.*—3 cm.
*Size.*—Medium.
*Colour.*—When opening. Upper Side: Yellow 1 B7 at base turning to very deep red. Under side: Same as above but with slight bloom.

Flower:

*Shape.*—Flattish — cup shaped — slightly quartered.
*Diameter.*—10 cm on average.
*Colour.*—When opening. Upper side: Yellow 3 B8 at base turning to Very Deep Rose Pink 13 B6. Under side: Same as above. When blooming: Upper side — Very Pale Yellow 2 A4 at base turning to Deep Pink 10 A3. Under side: Pastel Yellow 2 A4 at base, turning to Rose Pink 13 B3 deepening to very Deep Rose Pink 13 B5 at centre. When finished blooming: Upper side: Cream 2 A2 at base turning to Rose Pink 13 A3. Under side: Cream 2 A2 at base turning to Rose Pink 13 A4.
*Fragrance.*—Strong and pleasant, old fashioned.
*Lasting quality.*—Good
*Petals.*—Shape — Spatulate. Texture — Slightly silky. Number — 66 on average. Cleaning — Good.

*Prickles.*—The prickles on the peduncles are sparse and slightly recurved at base to straight at the top. Colour — From reddish brown 11 D8 at base become in brown 7E 8 to the tip.

Reproductive organs:

*Stamens.*—Number — 86 on average. Anthers — Golden yellow. Filaments — Yellow.
*Pistils.*—Number — 79 on average. Stigmas — Yellow. Styles — Pale green. Finely hairy. Receptacle — Fairly shallow cup, Medium green in colour.

The development:

Vegetation.—Tall, dense and bushy.
*Blooming.*—Continual.
*Aptitude to bear fruits.*—normal.
*Resistance to frost.*—Good.
*Resistance to diseases.*—Good.

I claim:

1. A new and distinct variety of rose plant of the shrub class, characterised as to novelty by its large double flowers with open centres exposing a bunch of golden stamens with abundant and continual blooming the unusual blend of colouring and shaping of the flower being substantially as shown and described.

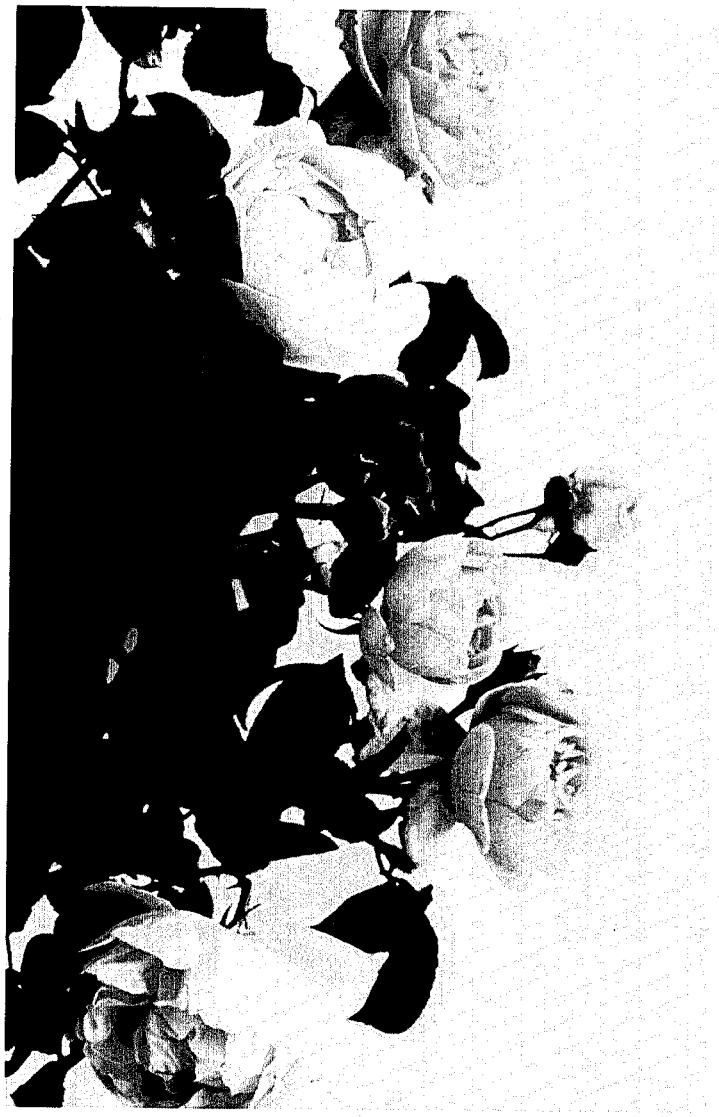

* * * * *